US012102715B1

(12) United States Patent
Kam et al.

(10) Patent No.: US 12,102,715 B1
(45) Date of Patent: Oct. 1, 2024

(54) ROS-RESPONSIVE LIPOSOMES FOR SPECIFIC TARGETING

(71) Applicant: Verily Life Sciences LLC, South San Francisco, CA (US)

(72) Inventors: Kimberly Kam, Orinda, CA (US); Zhan Wang, San Jose, CA (US); Stephen Morton, Mountain View, CA (US); Nicole Peck, Redwood City, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 396 days.

(21) Appl. No.: 17/532,795

(22) Filed: Nov. 22, 2021

Related U.S. Application Data

(62) Division of application No. 16/690,599, filed on Nov. 21, 2019, now Pat. No. 11,179,335, which is a division of application No. 15/672,591, filed on Aug. 9, 2017, now Pat. No. 10,517,823.

(60) Provisional application No. 62/372,990, filed on Aug. 10, 2016.

(51) Int. Cl.
| | |
|---|---|
| *A61K 9/127* | (2006.01) |
| *A61K 31/7088* | (2006.01) |
| *A61K 38/02* | (2006.01) |
| *A61K 39/395* | (2006.01) |
| *A61K 47/42* | (2017.01) |
| *A61K 47/69* | (2017.01) |
| *A61K 49/00* | (2006.01) |
| *A61P 39/06* | (2006.01) |
| *B01J 13/22* | (2006.01) |

(52) U.S. Cl.
CPC .......... *A61K 9/1271* (2013.01); *A61K 9/1277* (2013.01); *A61K 31/7088* (2013.01); *A61K 38/02* (2013.01); *A61K 39/395* (2013.01); *A61K 47/42* (2013.01); *A61K 47/6913* (2017.08); *A61K 49/0032* (2013.01); *A61K 49/0086* (2013.01); *A61P 39/06* (2018.01); *B01J 13/22* (2013.01); *Y10S 977/773* (2013.01); *Y10S 977/906* (2013.01); *Y10S 977/907* (2013.01)

(58) Field of Classification Search
CPC .............................. A61K 9/127; A61K 9/1271
See application file for complete search history.

(56) References Cited

U.S. PATENT DOCUMENTS

| | | | | |
|---|---|---|---|---|
| 3,130,009 | A | | 4/1964 | Brotherton |
| 5,891,468 | A | * | 4/1999 | Martin ..................... A61P 35/00 436/829 |
| 10,106,650 | B2 | | 10/2018 | Lam et al. |
| 10,517,823 | B1 | * | 12/2019 | Kam ..................... A61K 39/395 |
| 10,583,083 | B1 | | 3/2020 | Wang et al. |
| 11,179,335 | B1 | * | 11/2021 | Kam ........................ B01J 13/22 |
| 2006/0153907 | A1 | | 7/2006 | Zalipsky et al. |
| 2007/0116753 | A1 | | 5/2007 | Hong et al. |
| 2007/0207489 | A1 | * | 9/2007 | Pestano ................ C12Q 1/6886 435/6.12 |
| 2009/0175873 | A1 | | 7/2009 | Liu |
| 2010/0298742 | A1 | * | 11/2010 | Perlman .................. A61B 5/746 600/595 |
| 2012/0058177 | A1 | | 3/2012 | Reisfeld et al. |
| 2013/0296224 | A1 | * | 11/2013 | Braiman-Wiksman ...................... C07K 7/06 514/6.9 |
| 2014/0308212 | A1 | | 10/2014 | Zhang |
| 2015/0342883 | A1 | | 12/2015 | Cheng et al. |

FOREIGN PATENT DOCUMENTS

CN 103755839 4/2014

OTHER PUBLICATIONS

Pamela R. Westmark, Stephen J. Gardiner, and Bradley D. Smith. "Selective Monosaccharide Transport through Lipid Bilayers Using Boronic Acid Carriers." Journal of the American Chemical Society, vol. 118, 1996, pp. 11093-11100. (Year: 1996).*
Yan Fang, Jianxiu Xue, Shan Gao, Anqi Lu, Dongjuan Yang, Hong Jiang, Yang He and Kai Shi. "Cleavable PEGylation: a strategy for overcoming the "PEG dilemma" in efficient drug delivery." Drug Delivery, vol. 24, No. 2, 2017, pp. 22-32. (Year: 2017).*
"Improving Drug Delivery with Macrophage Targeting", Olympus, May 16, 2013, 11 pages.
"Polypropylene Glycol", Available Online at: https://www.sigmaaldrich.com/catalog/product/aldrich/81380?lang=en&region=IN, Accessed from Internet on Aug. 5, 2019, 3 pages.
U.S. Appl. No. 15/672,589, Final Office Action, Mailed on May 14, 2019, 20 pages.
U.S. Appl. No. 15/672,589, Non-Final Office Action, Mailed on Jan. 17, 2019, 14 pages.
U.S. Appl. No. 15/672,589, Non-Final Office Action, Mailed on Aug. 13, 2019, 17 pages.
U.S. Appl. No. 15/672,591, Final Office Action, Mailed on May 6, 2019, 13 pages.
U.S. Appl. No. 15/672,591, Non-Final Office Action, Mailed on Jan. 23, 2019, 15 pages.
U.S. Appl. No. 16/690,599, Non-Final Office Action, Mailed on Mar. 12, 2021, 17 pages.
U.S. Appl. No. 16/750,910, Non-Final Office Action, Mailed on Jul. 15, 2021, 13 pages.
U.S. Appl. No. 16/750,910, Non-Final Office Action, Mailed on Apr. 9, 2021, 14 pages.

(Continued)

*Primary Examiner* — Isaac Shomer
(74) *Attorney, Agent, or Firm* — Kilpatrick Townsend & Stockton

(57) ABSTRACT

Provided herein are encapsulated liposomes comprising a lipid bilayer, a first polyethylene glycol (PEG) corona, a targeting molecule and a second PEG corona. The second, encapsulating PEG corona can be reversibly linked to the first PEG corona. Also provided are pharmaceutical compositions comprising the encapsulated liposomes and methods of treating a subject with a disease characterized by production of reactive oxygen species (ROS) with the compositions. Also provided are methods of making the encapsulated liposomes disclosed herein.

4 Claims, 2 Drawing Sheets

(56) References Cited

OTHER PUBLICATIONS

Akbarzadeh et al., "Liposome: Classification, Preparation, and Applications", Nanoscale Research Letters, vol. 8, No. 1, Feb. 22, 2013, 9 pages.
Allen et al., "Anti-CD19-Targeted Liposomal Doxorubicin Improves the Therapeutic Efficacy in Murine B-Cell Lymphoma and Ameliorates the Toxicity of Liposomes with Varying Drug Release Rates", Clin Cancer Res., Cancer Therapy: Preclinical, vol. 11, No. 9, May 1, 2005, pp. 3567-3573.
Alli et al., "Synthesis, Characterization and Surface Properties of Amphiphilic Polystyrene-B-Polypropylene Glycol Block Copolymers", European Polymer Journal, vol. 42, Issue 4, Apr. 2006, pp. 740-750.
Amoozgar et al., "Targeting Myeloid Cells Using Nanoparticles to Improve Cancer Immunotherapy", Advanced Drug Delivery Reviews, vol. 91, Aug. 30, 2015, pp. 38-51.
Ashley et al., "Liposomal Bortezomib Nanoparticles via Boronic Ester Prodrug Formulation for Improved Therapeutic Efficacy in Vivo", Journal of Medicinal Chemistry, vol. 57, Issue 12, Jun. 26, 2014, pp. 5282-5292.
Boomer et al., "Cytoplasmic Delivery of Liposomal Contents Mediated by an Acid-Labile Cholesterol-Vinyl Ether-PEG Conjugate", Bioconjug. Chemistry, vol. 20, No. 1, Jan. 2009, pp. 47-59.
Bozzuto et al., "Liposomes as Nanomedical Devices", International Journal of Nanomedicine, Dovepress, vol. 10, Feb. 2, 2015, pp. 975-999.
Bull et al., "Exploiting the Reversible Covalent Bonding of Boronic Acids: Recognition, Sensing, and Assembly", Accounts of Chemical Research, vol. 46, No. 2, Feb. 19, 2013, pp. 312-326.
Charrois et al., "Drug Release Rate Influences the Pharmacokinetics, Biodistribution, Therapeutic Activity, and Toxicity of Pegylated Liposomal Doxorubicin Formulations in Murine Breast Cancer", Biochimica et Biophysica Acta, vol. 1663, No. 1-2, www.sciencedirect.com, May 27, 2004, pp. 167-177.
Chawla et al., "Macrophage-Mediated Inflammation in Metabolic Disease", Nature Reviews. Immunology, vol. 11, No. 11, Oct. 10, 2011, pp. 738-749.
Cummings et al., "Tetrahydroxydiboron-Mediated Palladium-Catalyzed Transfer Hydrogenation and Deuteration of Alkenes and Alkynes Using Water as the Stoichiometric H or D Atom Donor", Journal of the American Chemical Society, vol. 138, No. 9, May 2016, pp. 6107-6110.
Daniels et al., "Dual-Responsive Nanoparticles Release Cargo Upon Exposure to Matrix Metalloproteinase and Reactive Oxygen Species", Chemical Communications, vol. 52, Issue 10, Feb. 4, 2016, pp. 2126-2128.
Dasgupta et al., "Non Inflammatory Boronate Based Glucose-Responsive Insulin Delivery Systems", PloS One, vol. 7, No. 1: e29585, 2012, 11 pages.
Davis et al., "Nanoparticle Therapeutics: An Emerging Treatment Modality for Cancer", Nature Reviews. Drug discovery, vol. 7, No. 9, Sep. 2008, pp. 771-782.
Etzerodt et al., "CD163 and Inflammation: Biological, Diagnostic, and Therapeutic Aspects", Antioxidants & Redox Signaling, vol. 18, Issue 17, 2013, pp. 2352-2363.
Fang et al., "Cleavable PEGylation: A Strategy for Overcoming the "PEG Dilemma" in Efficient Drug Delivery", Drug Delivery, vol. 24, No. 2, Dec. 2017, pp. 22-32.
Germano et al., "Role of Macrophage Targeting in the Antitumor Activity of Trabectedin", Cancer cell, vol. 23, No. 2, Feb. 11, 2013, pp. 249-262.
Graversen et al., "Drug Trafficking Into Macrophages via the Endocytotic Receptor CD163", Membranes, vol. 5, No. 2, Jun. 23, 2015, pp. 228-252.
Grosse et al., "Tumor-Specific Gene Transfer With Receptor-Mediated Nanocomplexes Modified by Polyethylene Glycol Shielding and Endosomally Cleavable Lipid and Peptide Linkers", The FASEB Journal, vol. 24, No. 7, Jul. 2010, pp. 2301-2313.

Irvine et al., "Synthetic Nanoparticles for Vaccines and Immunotherapy", Chemical reviews, vol. 115, No. 19, Oct. 14, 2015, pp. 11109-11146.
Israelachvili et al., "Physical Principles of Membrane Organization", Quarterly Reviews of Biophysics, vol. 13, No. 2, 1980, pp. 121-200.
Jeong et al., "Reactive Oxygen Species Responsive Drug Releasing Nanoparticle Based on Chondroitin Sulfate-Anthocyanin Nanocomplex for Efficient Tumor Therapy", Journal of Controlled Release, vol. 222, Jan. 2016, pp. 78-85.
Joo et al., "Crosslinked Multilamellar Liposomes for Controlled Delivery of Anticancer Drugs", Biomaterials, vol. 34, No. 12, Apr. 2013, pp. 3098-3109.
Larkin et al., "Structure of the Boronic Acid Dimer and the Relative Stabilities of Its Conformers", Journal of Physical Chemistry A, vol. 110, No. 36, Sep. 14, 2006, pp. 10633-10642.
Li et al., "Boronate-Dextran: An Acid-Responsive Biodegradable Polymer for Drug Delivery", Biomaterials, vol. 34, No. 33, Nov. 2013, pp. 8504-8510.
Liang et al., "ROS-Responsive Drug Delivery Systems", Bioengineering & Translational Medicine, vol. 1, No. 3, Sep. 2016, pp. 239-251.
Liu et al., "Codelivery of Doxorubicin and Paclitaxel by Cross-Linked Multilamellar Liposome Enables Synergistic Antitumor Activity", Molecular Pharmaceutics, vol. 11, Issue 5, 2014, pp. 1651-1661.
Liu et al., "Legumain Protease-Activated TAT-Liposome Cargo for Targeting Tumours and their Microenvironment", Nature Communications, vol. 5. No. 4280, Jun. 27, 2014, 11 pages.
Love et al., "Efficient Clodronate Entrapment Within Multilamellar and Unilamellar Liposomes", Journal of Pharmacological and Toxicological Methods, vol. 27, No. 3, May 1992, pp. 185-189.
Lux et al., "Biocompatible Polymeric Nanoparticles Degrade and Release Cargo in Response to Biologically Relevant Levels of Hydrogen Peroxide", Journal of the American Chemical Society, vol. 134, No. 38, Sep. 4, 2012, pp. 15758-15764.
Matsumoto et al., "Safe Control of Construction-Deconstruction of High-Density Peg Brushes on the Surface of Peptide Nanospheres by Thermally Induced Shrinkage of PEG-SS-PEG", Chemistry Letters, vol. 42, 2013, pp. 344-346.
Matsumoto et al., "Safe Control of Construction-Deconstruction of High-Density PEG Brushes on the Surface of Peptide Nanospheres by Thermally Induced Shrinkage of PEG-SS-PEG", Supporting Information, Chemistry Letters, vol. 42, No. 4, 2013, pp. 1-10.
Minikel, "Organic Chemistry 08: Carbonyl Conjugation, Conformational Analysis, Cyclic Compounds", Available Online at: www.cureffi.org/2015/02/13/organic-chemistry-08/, Feb. 13, 2015, 9 pages.
Mo et al., "Tumor Microenvironment and Intracellular Signal-Activated Nanomaterials for Anticancer Drug Delivery", Materials Today, vol. 19, No. 5, pp. 274-283, Jun. 2016.
Moon et al., "Interbilayer-Crosslinked Multilamellar Vesicles as Synthetic Vaccines for Potent Humoral and Cellular Immune Responses", Nature materials, vol. 10, No. 3, Mar. 2011, pp. 243-251.
Murray et al., "Protective and Pathogenic Functions of Macrophage Subsets", Nature Reviews Immunology, vol. 11, No. 11, Nov. 2011, pp. 723-737.
Rowan et al., "Dynamic Covalent Chemistry", Angewandte Chemie International Edition, vol. 41, No. 6, Mar. 15, 2002, pp. 899-952.
Ruffell et al., "Macrophages and Therapeutic Resistance in Cancer", Cancer cell, vol. 27, No. 4, Apr. 13, 2015, pp. 462-472.
Saravolac et al., "Effect of Liposome-Encapsulation on Immunomodulating and Antiviral Activities of Interferon-Gamma 1", Antiviral research, vol. 29, Mar. 1996, pp. 199-207.
Sforzi et al., "Liposome-Based Bioassays", Biology, vol. 9, No. 202, 2020, pp. 1-25.
Shim et al., "A Reactive Oxygen Species (ROS)-Responsive Polymer for Safe, Efficient, and Targeted Gene Delivery in Cancer Cells", Angewandte Chemie International Edition, vol. 52, No. 27, Jul. 1, 2013, pp. 6926-6929.
Sun et al., "The Mechanisms of Boronate Ester Formation and Fluorescent Turn-On in Ortho-Aminomethylphenylboronic Acids", Nature Chemistry, vol. 11, No. 9, Sep. 2019, pp. 768-778.

(56) References Cited

OTHER PUBLICATIONS

Suzuki, "Recent Advances in the Cross-Coupling Reactions of Organoboron Derivatives with Organic Electrophiles, 1995-1998", Journal of Organometallic Chemistry, vol. 576, No. 1-2, Mar. 15, 1999, pp. 147-168.

Takeshima et al., "Ratiometric Sensing of Hydrogen Peroxide Utilizing Conformational Change in Fluorescent Boronic Acid Polymers", Journal of Analytical Methods in Chemistry, vol. 2017, Article ID 7829438, Sep. 28, 2017, 7 pages.

Tang et al., "A Detachable Coating of Cholesterol-Anchored Peg Improves Tumor Targeting of Cell-Penetrating Peptide-Modified Liposomes", Acta Pharmaceutica Sinica B., vol. 4, No. 1, Feb. 2014, pp. 67-73.

Terada et al., "Novel PEG-Matrix Metalloproteinase-2 Cleavable Peptide-Lipid Containing Galactosylated Liposomes for Hepatocellular Carcinoma-Selective Targeting", Journal of Controlled Release, vol. 111, No. 3, Apr. 10, 2006, pp. 333-342.

Voccia et al., "Improving Impedimetric Nucleic Acid Detection by using Enzyme-Decorated Liposomes and Nanostructured Screen-Printed Electrodes", vol. 408, 2016, pp. 7271-7281.

Wilson et al., "Orally Delivered Thioketal-Nanoparticles Loaded With TNFα-siRNA Target Inflammation and Inhibit Gene Expression in the Intestines", Nature materials, vol. 9, No. 11, Nov. 2010, pp. 923-928.

Zhang et al., "Biocompatible Reactive Oxygen Species (ROS)-Responsive Nanoparticles as Superior Drug Delivery Vehicles", Advanced healthcare materials, vol. 4, Issue 1, Jan. 7, 2015, pp. 69-76.

Zhao et al., "Boronic Acid Shell-Crosslinked Dextran-b-PLA Micelles for Acid-Responsive Drug Delivery", Macromolecular Bioscience, vol. 14, No. 11, Nov. 2014, pp. 1609-1618.

* cited by examiner

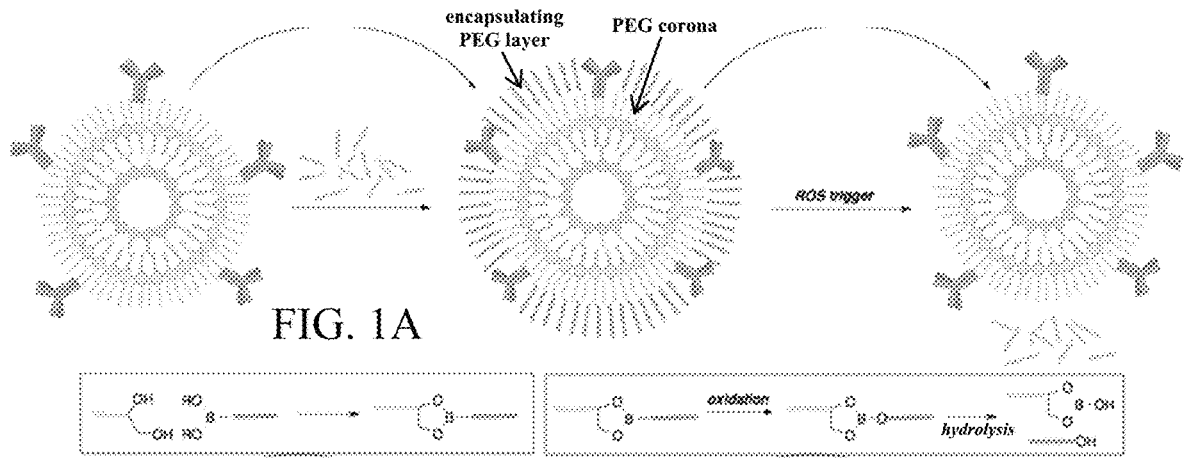
FIG. 1A
FIG. 1B
FIG. 1C
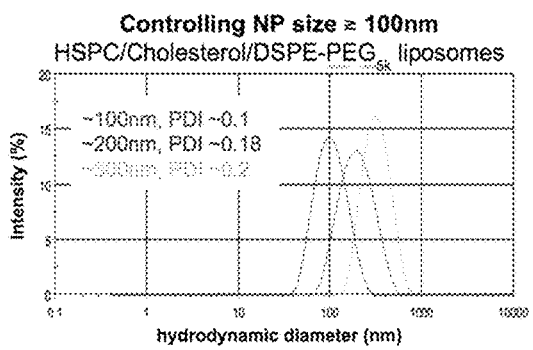
FIG. 2A
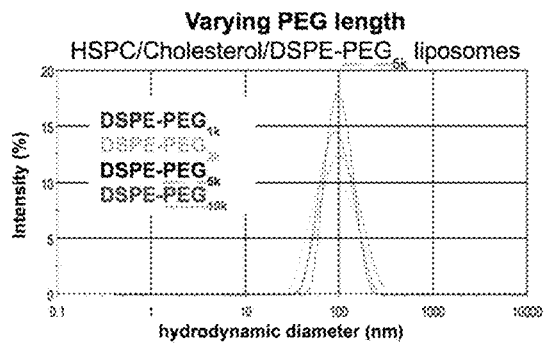
FIG. 2B

ROS-RESPONSIVE LIPOSOMES FOR SPECIFIC TARGETING

CROSS-REFERENCE TO RELATED APPLICATIONS

This application is a Divisional of U.S. patent application Ser. No. 16/690,599 filed Nov. 21, 2019, which is a Divisional of U.S. patent application Ser. No. 15/672,591 filed Aug. 9, 2017, which claims priority to U.S. Provisional Application No. 62/372,990, filed Aug. 10, 2016, each of which are incorporated by reference herein in their entirety.

BACKGROUND

Specific targeting with therapeutic agents offers substantial advantages but, to date, has proven challenging. Therapeutic agents can be passively targeted with nanoparticles, like liposomes, using the enhanced permeation and retention (EPR) effect. Tumors, for example, have permeable vasculature, which provides for enhanced growth of the blood supply, and passive targeting can be utilized. Active targeting using nanoparticles with a therapeutic agent and targeting moiety can concentrate effects in specific organs, tissues, and/or cell types, reduce degradation of the therapeutic agents, and reduce the toxic effects of systemic administration of the therapeutic agent. The targeted nanoparticles can be PEGylated, which increases circulation time of administered nanoparticles. However, constructing a PEGylated nanoparticle with active targeting has proven challenging because targeting moieties must be accessible for molecular recognition but surface-accessible targeting moieties may be degraded or lost. Additionally presenting targeting moieties on the surface of a particle may decrease the ability of the particle to evade clearance systems and thus may result in decreased in vivo half-life of the nanoparticles. Further, nanoparticles with targeting molecules formulated for oral delivery must be stable in the presence of stomach acid.

SUMMARY

Provided herein are encapsulated liposomes comprising a lipid bilayer, a first polyethylene glycol (PEG) corona, a targeting molecule and a second PEG corona. The second, encapsulating PEG corona can be reversibly linked to the first PEG corona. Also provided are pharmaceutical compositions comprising the encapsulated liposomes and methods of treating a subject with a disease characterized by production of reactive oxygen species (ROS) with the compositions. Also provided are methods of making the encapsulated liposomes disclosed herein.

BRIEF DESCRIPTION OF THE DRAWINGS

FIGS. 1A, 1B, and 1C are schematics showing the synthesis of ROS-triggered PEG-sheddable liposomes and the ROS-triggered release of the encapsulating PEG layer. FIG. 1A is a schematic showing an exemplary embodiment of formation of an encapsulated liposome and release of the encapsulating PEG layer. FIG. 1B is a schematic showing an exemplary embodiment in which a first PEG containing a terminal boronate moiety is attached to a second PEG containing a terminal hydroxyl moiety. FIG. 1C is a schematic showing an exemplary embodiment in which two PEG molecules reversibly linked by a boronic ester bond are unlinked by oxidation and hydrolysis of the boronic ester bond.

FIG. 2A is a graph showing the size distribution of liposomal formulations with an exemplary composition of HSPC:Cholesterol:DSPE-PEG. FIG. 2B is a graph showing varying composition (PEG length) for a given desired size range, 100 nm.

DETAILED DESCRIPTION

Figure 3:
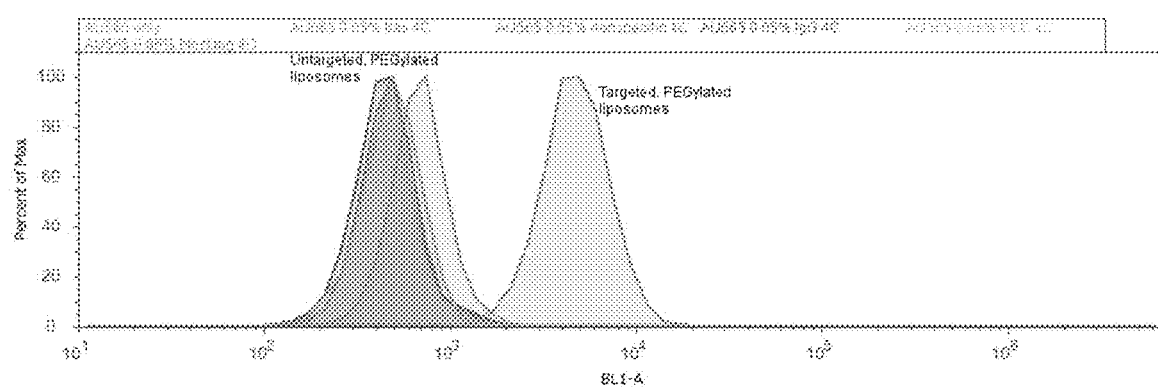
FIG. 3 is a graph showing levels of fluorescence indicating binding of targeted liposomes to cell lines as assessed by flow cytometry. Her2-targeted liposomes result in a significant shift in fluorescence versus the control of untargeted, PEGylated liposomes, indicating that the targeting liposomes are binding to the cells.

Provided herein are encapsulated liposomes that, in the presence of reactive oxygen species (ROS), shed or partially shed a polyethylene glycol (PEG) encapsulating layer, to reveal a liposome with a PEG corona and a targeting moiety. Specifically, the encapsulated liposome comprises a lipid bilayer with a first (PEG) corona, wherein the PEG corona further comprises a targeting molecule, and a, second, encapsulating PEG corona reversibly linked to the first PEG corona. Optionally, the encapsulated liposome further comprises one or more active agents. Optionally, the links between the first PEG corona and the second PEG corona are reversible in the presence of ROS. As used herein, the term reversible means the link or bond between the two molecules, e.g., between two PEG molecules, is impermanent and can allow the molecules to separate if the link is broken or reversed. The link or bond reacts in the presence of ROS to allow the two reversibly linked molecules to separate.

Specifically, provided herein are encapsulated liposomes having a first polyethylene glycol (PEG) corona reversibly linked to a second PEG corona. The second PEG corona or encapsulating PEG layer can partially or fully surround the liposome. Optionally, the second PEG corona fully surrounds the liposome. Optionally, the second PEG corona partially surrounds the liposome. The encapsulated liposome includes a targeting molecule that is fully or partially protected by the second PEG corona. The second, encapsulating PEG corona can be reversibly linked to the first PEG corona, for example, by boronic ester bonds, thioketal bonds, or other ROS reactive bonds. In the presence of ROS, the bonds can hydrolyze resulting in reversal of the links between the second PEG corona and the first PEG corona. Reversal of the link between the second PEG corona and the first PEG corona releases (or sheds) the second PEG corona. Upon release or shedding of the second PEG corona, the targeting molecule of the encapsulated liposome is partially or fully exposed. Thus, the second PEG corona protects the targeting molecule from degradation or loss until the encapsulated liposome reaches ROS-containing microenvironments. Upon release of the sheddable second PEG corona, the targeting molecule is capable of selectively binding a target of interest and, optionally, delivering one or more active agents to the target site. Thus, the encapsulated liposomes are useful for targeted delivery of one or more active agents to ROS-containing microenvironments, such as tumors. Because cancer cells and healthy cells express many of the same targets of interest, the ability to expose the targeting agents in ROS-containing microenvironments reduces toxic effects in healthy tissues and reduces degradation of the liposomes and targeting moieties.

Liposomes are vesicles consisting of amphipathic lipids arranged in one or more bilayers. When lipids are placed in aqueous medium, the hydrophilic interaction of the lipid head groups with water results in the formation of multilamellar or unilamellar systems or vesicles which resemble biological membranes in the form of a spherical shell. Liposomes may be small (0.025-0.05 µm) to large (0.05-10 µm). Optionally, the liposomes have diameters of 50-5,000 nm or less. Thus, liposomes can be unilamellar (having one lipid bilayer) or multilamellar (having two or more lipid bilayers) and a population of encapsulated liposomes can contain both unilamellar and multilamellar liposomes. See, e.g., Akbarzadeh et al., *Nanoscale Res. Letters,* 8:102-110 (2013), which is incorporated by reference herein in its entirety. As used herein, an inner cavity refers to the space inside a lipid bilayer of a liposome. As used herein, an interbilayer (interlamellar) space defines the region between two lipid bilayers. In a multilamellar liposome, for example, having three lipid bilayers, the inner cavity would be the space within the first (inner-most) lipid bilayer, an interbilayer space between the first and second (middle) lipid bilayers, and another interbilayer space between the second and third (outer-most) lipid bilayers.

Liposomes have one or more lipid bilayers, each bilayer having two layers of amphiphilic molecules such as lipids. The hydrophobic portions of the amphiphilic molecules of both layers project towards each other, minimizing contact with aqueous environments. The hydrophilic portions of the amphiphilic molecules form an interface with the surrounding aqueous environment. Lipids used to prepare liposomal lipid bilayers can include, but are not limited to, phospholipids, sphingolipids, glycosphingolipids, saturated glycerides, steroids such as cholesterol, synthetic phospholipids, and combinations thereof. Optionally, one or more lipids in the lipid bilayer contains a hydroxyl group, diol or triol groups. Optionally, the lipids comprise hydrogenated soy phosphatidylcholine (HSPC), distearoyl glycerol phosphoethanolamine (DSPE), or combinations thereof. The lipids of the lipid bilayer can include one or more different types of lipids. Thus, for example, the lipid bilayer can include both HSPC and DSPE. Optionally, the lipid bilayer comprises two or more types of lipids. Optionally, each of the two or more types of lipids are located in proximity to each other. Thus, lipids of a certain type may be located in proximity to each other in a lipid bilayer to form, for example, lipid islands. As used herein, the term lipid island refers to a group of lipids of the same type, e.g., DSPE, located in proximity to each other, e.g., aggregated, and surrounded by lipids of a different type, e.g., HSPC. Optionally, the liposomes include HSPC, cholesterol and lipid islands comprising PEG attached to the lipid DSPE (DSPE-PEG). It is understood that the hydrocarbon chains of any of the lipids can be of the same or differing lengths.

Liposomal lipid bilayers may contain one or more components in addition to the lipids. Optionally, the additional components can include, but are not limited to, detergents, protein-conjugated molecules, and molecules with aliphatic anchors. The additional components may be inserted into lipid bilayers by, for instance, hydrophobic interaction, non-covalent attachment to lipid bilayers, or covalent attachment to lipid bilayers by, for instance, bond formation with lipid head groups. The additional components in the liposomal lipid bilayers may alter the properties of lipid bilayers, including but not limited to, changing membrane fluidity, permeability, flexibility, fusogenicity, stability, charge/electrostatics, symmetry, cellular uptake, and the like. By way of example, addition of cholesterol to fluid lipid bilayers decreases permeability and fluidity of the liposome. See e.g., Bozzuto et al., *Intl J. of Nanomedicine,* 10: 975-999 (2015), which is incorporated herein by reference in its entirety.

Methods for making liposomes are known. For example, liposomes may be prepared by dissolving lipids in a solvent, which may optionally contain an emulsifier, followed by drying to form a thin lipid film. The lipid film is then hydrated to form sheets of lipid bilayers. Using hydration and agitation or sonication, for example, the lipid bilayers form spherical lipid bilayers. Fusion, extrusion, solvent addition, freeze-thaw, detergent removal, or further agitation may be used, as desired, to control liposome homogeneity in size and lamellarity. For instance, extrusion and sonication may result in unilamellar liposomal vesicles. Liposomes comprising a lipid bilayer including one or more PEG molecules and a targeting molecule can be made by any method known. See, e.g., Bozzuto et al., *Intl J. of Nanomedicine,* 10: 975-999 (2015); Akbarzadeh et al., *Nanoscale Res. Letters,* 8:102-110 (2013), which are incorporated herein in their entireties.

The first PEG corona, targeting agent, second PEG corona and/or active agent can be added to the liposome after the liposome is formed or during formation of the liposome. Thus, provided herein are methods of making the encapsulated liposome disclosed herein. The method optionally includes providing a liposome comprising a lipid bilayer with a first PEG corona, wherein the first PEG corona further comprises a targeting molecule; and contacting the liposome with a linker and PEG molecules, under conditions for forming a liposome with a second PEG corona reversibly linked to the first PEG corona. Also provided is a method of making an encapsulated liposome by providing a liposome comprising a lipid bilayer and a targeting molecule; and contacting the liposome with reversibly linked PEG molecules, under conditions for forming a liposome comprising a lipid bilayer, wherein the lipid bilayer comprises the targeting molecule and a first PEG corona and wherein the first PEG corona is reversibly linked to a second PEG corona. As described above, the reversible link can be a boronic ester bond or a thioketal bond. Thus moieties for forming the boronic ester bond or a thioketal bond can bind during the contacting step or the reversibly linked PEG molecules can be provided to the liposome.

Similarly, additional components of the lipid bilayer or agents to be added to the inner cavity or interlamellar space(s) may be added during formation of encapsulated liposomes or added after formation of the liposomes. Thus, if the PEG or other components are added during formation of the liposome, they are added to the nascent liposomes (e.g., to the lipid solution, to the thin lipid film, to the sheet of lipid bilayer, or during hydration or sonication). The PEG chains will contain functional groups that enable the formation of the first PEG corona linked to the secondary, sheddable PEG corona. Optionally, the PEG is provided as both the first PEG chain conjugated to the secondary PEG chain by an ROS reactive bond.

Polyethylene glycol is a polymer of ethylene oxide and has a structure typically expressed as H—(O—CH$_2$—CH$_2$) n-OH. Thus, the term "PEG" refers to a polyethylene glycol, a linear, water-soluble polymer of ethylene PEG repeating units with two terminal hydroxyl groups. PEGs are commercially available from Sigma-Aldrich Chemical Co. and other companies. The first and second PEG coronas may be formed from any PEG molecule. The PEG molecules in the first PEG corona may be selected to accommodate a targeting molecule. Optionally, the PEGs in the PEG coronas have different lengths or chemical composition. Optionally, the PEGs in the PEG coronas have different molecular weights. Further, the first PEG corona could have one PEG attached to the lipid bilayer and/or targeting moiety and a different PEG attached to the second PEG corona. Optionally, the first or second PEG coronas include PEG molecules having a boronate moiety or a thioketal moiety at a terminal end and a hydroxyl moiety at a terminal end. The PEG molecules in the PEG corona may contain a moiety to which a targeting molecule is attached and, optionally, additional moieties (e.g., a moiety capable of forming a boronic or thioketal bond, e.g., a hydroxyl moiety). Optionally, the PEG coronas include branched PEG molecules.

As described herein, the encapsulated liposomes include a lipid bilayer with a first PEG corona, a targeting molecule, and a second, encapsulating PEG layer. Specifically, the first PEG corona comprises a targeting molecule, and the second, encapsulating PEG corona or layer is reversibly linked to the first PEG corona, which fully or partially surrounds the liposome and protects the targeting molecule. Optionally, the reversible links between the second PEG corona and the first PEG corona are boronic ester bonds or thioketal bonds. Reversal of the links between the first and second PEG coronas results in shedding or partial shedding of the second, encapsulating PEG corona or layer.

FIG. 1A shows an exemplary structural arrangement of the lipid bilayer, first PEG corona, targeting molecule, and second PEG corona of the encapsulated liposome. As shown in FIG. 1A, the lipid bilayer surrounds an inner space or inner cavity. The encapsulated liposome optionally contains an active agent, e.g., a therapeutic or diagnostic agent, which can be located in the inner cavity or within the lipid bilayer.

The first PEG corona is attached to the lipid bilayer. As used herein, the first PEG corona refers to PEG molecules attached to the outer surface of or inserted into the lipid bilayer of the encapsulated liposome. The PEG molecules of the first PEG corona may be attached to the lipid bilayer in a variety of ways. The PEG molecules may be inserted into the lipid bilayer of the liposome, having a hydrophobic moiety in the lipid bilayer, which stabilizes the PEG by hydrophobic interactions. Alternatively, the PEG molecules of the first PEG corona may be covalently attached to the lipid bilayer (e.g., to lipid head groups of the lipids) or to other molecules in the lipid bilayer (e.g. embedded sterols or proteins).

The second PEG corona or layer fully or partially surrounds the liposome. The second PEG corona is attached to the first PEG corona such that at least a portion of the PEG molecules of the second PEG corona are attached to the PEG of the first PEG corona. The middle diagram in FIG. 1A shows an exemplary embodiment of the attachment of the second PEG corona to the first PEG corona. For example, the second PEG corona is reversibly linked to the first PEG corona, and each encapsulated liposome can include a plurality of such linkages. As used herein, the term link or linkage refers to a covalent attachment bridging at least two complex molecules. Optionally, the links comprise boronic ester bonds or thioketal bonds between the PEG molecules of the second PEG corona and the first PEG corona. Each boronate moiety can form bonds with hydroxyl groups at the terminal ends of the PEG molecules. Each thioketal moiety can form direct bonds with two carbon atoms. FIG. 1B shows, as an example, links between the PEG molecules including boronic ester bonds. A linker or crosslinker having a boronate moiety (or thioketal moiety) reacts with PEG molecules having a group reactive to a boronate moiety (or thioketal moiety) to form a link, e.g., a boronic ester bond or a thioketal bond between two PEG molecules. Optionally, reversible links are located between a first PEG in the first PEG corona and a second PEG in the second PEG corona, for example, at terminal ends of the PEG molecules. Optionally, more than one PEG in the second PEG corona can be linked to a single PEG molecule in the first PEG corona. Optionally, more than one PEG in the first PEG corona can be linked to a single PEG in the second PEG corona. The links between the PEG molecules of the first PEG corona and the second PEG corona can include boronic ester bonds, thioketal bonds or a combination of boronic ester and thioketal bonds.

The link comprising one or more bonds may include a spacer between the one or more bonds. The spacer serves to link a first PEG in the first PEG corona and a second PEG in the second PEG corona. The spacer may be attached to the PEGs in the encapsulating layer and the corona by boronic ester bond and or a thioketal bond.

Linkers or crosslinkers that can be used to form boronic ester bonds and thioketal bonds include, but are not limited to, linkers that have a boronate moiety, a thioketal moiety, aryl boronic acids, phenylboronates, pyridylboronates, and cyclohexylboronates. Linkers that can be used to form the boronic ester bonds or thioketal bonds include, but are not limited to, 4-bromomethylphenyl boronic acid pinacol ester, 3-(N,N-dimethylamino)phenyl boronic acid; 2,4-dichlorophenylboronic acid; 4-aminocarbonylphenylboronic acid; 3-chlorophenylboronic acid; 4-hydroxyphenylboronic acid; 4-propylphenylboronic acid; 3-[(E)-2-nitrovinyl)phenylboronic acid; 4-chlorocarbonylphenylboronic anhydride; cyclopenten-1-ylboronic acid; 2-bromopyridine-3-boronic acid; 2,4-ditert-butoxypyrimidin-5-ylboronic acid; 2,4-bis (benzyloxy)pyrimidine-5-boronic acid; 5-phenyl-2-thienylboronic acid; 5-formylthiophene-3-boronic acid; $CH_2CHCONHCH_2CH_2SC(CH_3)_2SCH_2CH_2NHCOCHCH_2$; $CH_2CHCONHCH_2CH_2SC(CH_3)_2SCH_2CH_2NHCOCHCH_2$; $CH_2CHCONHCH_2CH_2SC(CH_3)_2SCH_2CH_2NHCOCHCH_2$; $CH'H''CHCONHCH_2CH_2SC(CH_3)_2 SCH_2CH_2NHCOCHCH''H'$; $CH_2CHCONHCH_2CH_2SC(CH_3)_2SCH_2CH_2NHCOCHCH_2$; $CH'H''CHCONHCH_2CH_2SC(CH_3)_2 SCH_2CH_2NHCOCHCH''H'$; $CH_2CHCONHCH_2CH_2SC(CH_3)_2SCH_2CH_2NHCOCHCH_2$; 3,3'-(propane-2,2-diylbis (sulfanediyl))dipropionic acid; or any combination thereof.

The encapsulated liposomes described herein include reversible links between PEGs in the first PEG corona and PEGs in the second PEG corona or between the PEGs and, optionally, spacers between the links as introduced according to the type of crosslinker employed. The boronic ester bonds and thioketal bonds are exemplary reversible links, which are ROS-responsive (i.e., the links are reversed in the presence of ROS). When the bonds are reversed, the second PEG corona or layer is released or partially released to expose or partially expose the targeting molecule. The reversible links can be reversed in the presence of ROS by oxidation and hydrolysis of the boronic ester bond or thioketal bond in the presence of ROS. FIG. 1C shows, as an example, the chemistry of a link formed by a boronic ester bond. In FIG. 1C, ROS such as hydrogen peroxide oxidizes the boronic ester bond. Oxidation of the boronic ester bond is followed by hydrolysis of the bond with water to release the PEG of the second, encapsulating PEG corona.

The linker can form a reversible link between the PEG molecules of the first PEG corona and the second PEG corona in several ways. For example, linkers and PEG molecules can be added to liposomes having a first PEG corona, such that the PEG molecules reversibly link to the PEG of the first PEG corona forming the second PEG corona. Optionally, PEG molecules and linkers are contacted with nascent liposomes (liposomes without the first PEG corona) such that the first and second PEG coronas or layers are formed in a single step. Optionally, PEG molecules are contacted with a linker to form linked PEG molecules, i.e., PEG-PEG molecules. The reversibly linked PEG-PEG molecules are then contacted with liposomes to form the first and second PEG coronas in a single step.

Optionally, a PEG may be synthesized to have a linker having one or more boronate moieties and/or one or more thioketal moieties attached. Optionally, the PEG molecules are attached to a crosslinker and the PEG-crosslinkers molecules are contacted with the liposomes having the PEG corona. Optionally, PEG molecules are contacted with liposomes having a PEG corona with PEG-crosslinker molecules.

A variety of methods can be used to make the encapsulated liposomes. For example, the reversibly linked PEG molecules may be inserted into the lipid bilayer of the liposome or may be covalently attached to the lipid bilayer, e.g. to lipid head groups of the lipids or to embedded sterols or proteins.

The encapsulated liposomes described herein include a targeting molecule. Targeting molecules provide specific delivery of a liposome or its cargo to a particular target of interest, e.g., protein, cell, tissue, or organ. Targeting molecules include, but are not limited to, antibodies or fragments thereof and aptamers having the desired function. Targeting molecules may include all or a fragment of an antibody conjugated to a second component. The second component can be a lipid, PEG or other molecule in the lipid bilayer and/or a linker, which links the targeting agent to the liposome. Thus, by way of example, the antibody or fragment can be directly or indirectly linked to the linker or to the lipid bilayer. The targeting molecule is protected until some or all of the second, encapsulating PEG corona is shed upon exposure to ROS. Optionally, the targeting molecule provides specific delivery of a liposome or its cargo to microenvironments containing ROS and potentially to a specific cell therein, e.g., a tumor cell. Optionally, the targeting molecule binds EGFR, EpCAM, HER2, folate receptor, folate hydrolase 1 (FOLH1), prostate-specific membrane antigen (PSMA). Thus, suitable targeting molecules include, but are not limited to, EGFR antibodies, HER2 antibodies, EpCAM antibodies, FolR antibodies, folate, trastuzumab, and PSMA antibodies.

As described herein, the encapsulated liposomes can include one or more active agents. Suitable active agents include, but are not limited to, nucleic acids, polypeptide, antibodies, small molecules, lipids, carbohydrates, and any combination thereof. The active agent or agents may be a therapeutic agent (e.g., a chemotherapeutic agent or phototherapeutic agent), a diagnostic agent, or any combination thereof. The encapsulated liposomes can include two or more active agents. The active agent or combination of active agents may be associated with the encapsulated liposome in one or more ways. Active agent or agents may be located in the inner cavity or within the interbilayer spaces of the encapsulated liposomes. Optionally, the active agent or agents may be located within the lipid bilayer or bilayers of the encapsulated liposomes. Optionally, the active agents are located within the inner cavity and/or interbilayer spaces and the lipid bilayer(s) of the encapsulated liposomes. Agents within the lipid bilayer are optionally partially or fully embedded therein. As used herein, the term embedded refers to the insertion of a hydrophobic portion of a molecule into the hydrophobic region of a lipid bilayer such that the inserted molecule is stabilized in the membrane at least partially by hydrophobic interactions. A fully embedded agent refers to an agent in which the entire structure of the agent is embedded within the hydrophobic region of a lipid bilayer. A partially embedded agent refers to an agent in which a portion of the agent is embedded within the hydrophobic region of a lipid bilayer and a portion of the agent is either embedded in the hydrophilic region of a lipid bilayer (e.g. in the lipid head groups) or protrudes from either surface of the lipid bilayer. Thus, active agents may be attached to the lipid bilayer, directly or indirectly using a linker.

Also described herein are pharmaceutical compositions comprising the encapsulated liposomes and a pharmaceutically acceptable excipient. The provided compositions are, optionally, suitable for formulation and administration in vitro or in vivo. Suitable carriers and excipients and their formulations are described in Remington: The Science and Practice of Pharmacy, 22nd Edition, Lloyd V. Allen, Jr., ed., Pharmaceutical Press (2012). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

The compositions for administration will commonly include the encapsulated liposomes and a pharmaceutically acceptable carrier, optionally an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 22nd Edition, Lloyd V. Allen, Jr., ed., Pharmaceutical Press (2012).

The provided compositions including the encapsulated liposomes can be used for treating a subject with a disease characterized by production of ROS. Thus, provided is a method of treating a disease characterized by production of ROS in a subject comprising administering to the subject an effective amount of an encapsulated liposome with a lipid bilayer with a first polyethylene glycol (PEG) corona, wherein the PEG corona further comprises a targeting molecule, a second PEG corona reversibly linked to the first PEG corona and one or more active agents, wherein administration treats the disease characterized by production of ROS. Optionally, a pharmaceutical composition including the encapsulated liposomes and a pharmaceutically acceptable excipient is administered to the subject. As used herein, a disease characterized by production of reactive oxygen species (ROS) means a disease or disorder in which ROS is produced in a subject having the disease. Production of ROS can be systemic or localized to a particular regions, organs, tissues, or cells (e.g., cancer cells or inflammatory macrophages). More specifically, the disease or disorder characterized by production of ROS can be cancer, an inflammatory disease, an autoimmune disease, or a neurodegenerative disease.

Compositions comprising the herein disclosed encapsulated liposomes can be delivered to a subject in a variety of ways, including intravenously, intramuscularly, subcutaneously, intraperitoneally, inhalation, intubation, topically, orally, local injection, or the like. If the encapsulated liposomes are administered in more than one dose, the encapsulated liposomes may be administered by the same or by different delivery methods.

The encapsulated liposomes or composition containing the liposomes may be administered locally or systemically. When the administered encapsulated liposome compositions is administered systemically, they may circulate and remain intact until they encounter a ROS-rich environment, where the boronic ester or thioketal links are reversed. The second PEG corona may act to stabilize the liposome (including the targeting moiety and the active agent), to reduce clearance, and to avoid systemic toxicity of the agent. When the reversible bonds are reversed and the second PEG corona is released or shed, partially or completely, the active agents is optionally released in the presence of ROS and/or upon binding of the targeting molecule to a target of interest.

Optionally, in the method of treatment, encapsulated liposomes may pass through the walls of tumor vessels and concentrate in tumors by passive targeting (enhanced permeation retention effect). Optionally, targeting moieties may be used for active targeting. In the method of treatment, the reversal of the links occur in vivo in the presence of ROS. Tumor microenvironments contain high levels of inducible nitric oxide synthase (iNOS), which results in increased concentrations of ROS such as peroxide, hydroxyl radical, and nitric oxide.

The targeting moiety and active agents, as described above, can be selected as desired for use in a method of treatment. The methods of treating a subject may optionally include administering to a subject an encapsulated liposome containing a phototherapeutic agent, for example, a phototherapeutic agents that stimulates local production of ROS. Indocyanine green is an FDA-approved fluorescent dye used for imaging to evaluate cardiac functions, liver functions, and other purposes. Stimulation of indocyanine green with light increases local production of ROS. Thus, the method of treatment optionally includes stimulating the phototherapeutic agent, for example, at the target site, such as a tumor.

As used herein, the term treat refers to any delay in onset or one or more symptoms or clinical signs, reduction in the frequency or severity of symptoms, amelioration of symptoms, improvement in patient comfort or function, decrease in severity of the disease state, etc. The effect of treatment can be compared to an individual or pool of individuals not receiving a given treatment, or to the same patient prior to, or after cessation of, treatment. Treatment includes partial or complete ablation of the disease. The term "prevent" generally refers to a decrease in the occurrence of a given disease (e.g., a primary cancer or metastasis). Prevention may be complete (no detectable symptoms) or partial, such that occurrence is delated or results in fewer symptoms than would occur absent treatment.

By effective dose or amount as used herein is meant a dose of liposomes or composition containing the liposomes that produces the desired effect(s) (e.g., treating or preventing a disease). The exact dose and formulation of the liposomes will depend on the purpose of the treatment and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington (2005); and Pickar, Dosage Calculations ($9^{th}$ edition) (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The exact dose, formulation, and dosing regimen of the encapsulated liposomes will depend on a number of factors including the purpose of the treatment, the species of the subject, the age and weight of the subject, the disease to be treated, the severity of the disease, the amount and type of active agent in the liposomes, and the like. Determining the dosage, formulation and dosing regimen are ascertainable by one skilled in the art using known techniques. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). Thus, treatment may include administering a single dose or multiple dose of the encapsulated liposomes or compositions containing liposomes. The encapsulated liposomes or composition containing the liposomes, as disclosed herein, can be administered to the subject on a daily, twice daily, bi-weekly, monthly or any effective regimen. The treatment can be administered alone or in combination with any other treatment modalities or agents. The additional treatment can be administered simultaneously with the first treatment, at a different time, or on an entirely different therapeutic schedule (e.g., the first treatment can be daily, while the additional treatment is weekly).

As used herein, the term cancer refers to any type of cancer including neoplasms or tumors, lymphoma, or leukemia characterized by the production of ROS. Non-limiting, exemplary cancers include cancer of the brain (e.g., astrocytoma, medulloblastoma, glioma, neuroblastoma), breast, cervix, esophagus, colon, head and neck, liver, kidney, lung, skin (e.g., melanoma), mesothelium, ovary, testes, bone, stomach, pancreas, bladder, thyroid, adrenal, prostate, and uterus. Additional examples include lymphoma (e.g., Hodgkin's Disease, non-Hodgkin's lymphoma), multiple myeloma, neuroblastoma, sarcoma (e.g., rhabdomyosarcoma).

Inflammatory diseases and autoimmune diseases include, but are not limited to, asthma, arthritis (e.g., rheumatoid or osteoarthritis), gout, cardiovascular disease, diabetes, lupus erythematosus, scleroderma, Sjorgen's syndrome, osteomyelitis, hepatitis, colitis, psoriasis, chronic obstructive pulmonary disease, bronchiectasis, emphysema, silicosis, inflammatory bowel disease, ulcerative colitis, Crohn's disease, multiple sclerosis, Guillain-Barre Syndrome, myasthenia gravis, mastitis, laminitis, laryngitis, chronic cholecystitis, Hashimoto's thyroiditis.

Neurodegenerative diseases include for example dementias (e.g., Alzheimer's disease, frontotemporal dementia), Parkinson's disease, Huntington's disease, multiple sclerosis, amyotrophic lateral sclerosis, Guillain-Barré syndrome, and the like.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Optionally, the provided encapsulated liposomes or compositions comprising the encapsulated liposomes contain an active agent and are used for diagnosing a disease characterized by production of ROS in a subject. Thus, provided is a method of diagnosing a disease in a subject comprising administering to the subject an effective amount of the provided encapsulate liposomes comprising a diagnostic agent or composition comprising the provided encapsulated liposomes comprising the diagnostic agent. Administration of the encapsulated liposomes or compositions diagnoses the disease or one or more symptoms of the disease in the subject. The disclosed methods involve comparing the levels or activity of a biomarker, e.g., intracellular target of a disease, from a test sample to a control sample. As discussed above, a control sample or value refers to a sample that serves as a reference, usually a known reference, for comparison to a test sample. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. As also discussed above, diagnosis refers to a relative probability that a disease (e.g. an autoimmune, inflammatory autoimmune, cancer, infectious, immune, or other disease) is present in the subject.

The terms comparing, correlating and associated, in reference to determination of a disease risk factor, refers to comparing the presence or amount of the risk factor (e.g., amount of intracellular target of a disease) in an individual to its presence or amount in persons known to suffer from, or known to be at risk of disease, or in persons known to be free of disease, and assigning an increased or decreased probability of having/developing the disease to an individual based on the assay result(s).

Also described herein are kits comprising the disclosed encapsulated liposomes or pharmaceutical compositions thereof. The kit comprises one or more dosage units of encapsulated liposomes having a first PEG corona and a second PEG corona or the pharmaceutical composition. Optionally, the kit comprises instructions for use, one or more additional agents, and/or devices for administering the liposomes or composition. Delivery devices include, but are not limited to, syringes, drip bags, patches, and inhalers. The kit may comprise a solution for reconstituting or diluting the liposomes or composition of liposomes. For example, if a disclosed composition is provided in a solid form that is to be reconstituted for parenteral administration, the kit can comprise a sealed container of a suitable solution in which the disclosed composition can be dissolved to form a liposome-containing solution suitable for parenteral administration. Examples of acceptable solutions include, but are not limited to: water sodium chloride solution, Ringer's, dextrose, dextrose and sodium chloride, and lactated Ringer's.

Disclosed are materials, compositions, and components that can be used for, can be used in conjunction with, can be used in preparation for, or are products of the disclosed methods and compositions. These and other materials are disclosed herein, and it is understood that, when combinations, subsets, interactions, groups, etc. of these materials are disclosed, that, while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. Formation of Encapsulated Liposomes

For organic dissolution and film preparation of lipids, heat-treated scintillation vials are prepared by storing 20 ml scintillation vials in oven at 230° C. for at least 2 hours prior to film preparation. 12 (+/−0.3) mg DPPE is added into a 20 mL scintillation vial (55% of total composition). 4 mg (400 µL) cholesterol is added from a stock solution of 10 mg/mL in 2:1 (v/v) mixture of chloroform:methanol to the 20 mL scintillation vial (39% of total composition). DSPE-PEG-X (where X is a diol, a thiol, an acetal precursor, a boronic ester with a second PEG, or a thioketal with a second PEG) is added such that a 5% molar ratio is established relative total composition. Optionally, 0.4 mg DPPE-Cy5.5 (tracker) is added from a stock solution of 1 mg/mL in 2:1 (v/v) mixture of chloroform:methanol to the 20 mL scintillation vial (0.01% of total composition). 0.5% DPPE-PEG-X where X is methyltetrazine, azide, TCO, DBCO, or other click chemistry moiety is added to the composition. 5 ml of 2:1 (v/v) mixture of chloroform:methanol is then added to the 20 mL scintillation vial. The lipid components should be fully dissolved. Then, the organic solvents are rotary evaporated off to form a uniform lipid film around the bottom of the 20 ml scintillation vial. A vacuum is used to pull slowly until a thin, uniform film remains. The vial is sealed with perforated parafilm and placed in dessicator for at least 2 hours to remove all volatile organics.

For lipid film hydration, 5 ml hydration buffer (freshly prepared 10 mM pH7.4 HEPES buffer—recipe below) is added to the 20 ml scintillation vial while sonicating under high heat. The sample is sonicated, vortexed, or shaken to obtain the desired size of liposome. For 200 nm or smaller liposomes, the hot mixture is extruded through filters of the desired size. The mixture is cooled to room temperature and diluted with PBS to 3 times the total volume. The particles are concentrated to approximately 3-4 mL total volume via spin filtration in 30 kDa MWCO filters.

For surface functionalization, antibodies or antibody fragments can be conjugated by incubating the functionalized liposomes with proteins that have been activated with the complementary click handle. For example, for a liposome that is functionalized with DSPE-PEG-Tz, a protein is used that has been modified specifically or nonspecifically with TCO, and the reaction is performed at room temperature with a protein final concentration of 1 µM for 16 hours. Unconjugated antibodies are removed by passing the liposomes through a SEC column using Sephacryl 400 resin. Fractions with high Cy5.5 fluorescence (if Cy5.5 was used as a fluorescent tag on the liposomes) are collected. To append a second PEG layer if the DSPE-PEG-X used previously did not already contain a second PEG chain, react the hydroxyl, diol, triol, thiol, or the like on the DSPE-PEG-X with boronic ester or thiol or acetal reactive PEG molecules.

Example 2. Testing the Efficacy of the Encapsulated Liposomes In Vivo or In Vitro Fluorophore-labeled, targeted liposomes were incubated with a cancer cell line expressing the targeted receptor, and flow cytometry was used to assess the binding. Non-targeted, PEGylated liposomes were used as a control. As shown in FIG. 3, PEGylated, HER2-targeted liposomes demonstrated the shift in fluorescence of the cells as a result of binding the fluorescence liposomes. Her2-targeted liposomes result in a significant shift in fluorescence vs. the control of untargeted, PEGylated liposomes, indicating that the targeting liposomes are binding to the cells.

To test for the effect of the ROS-triggered corona, a binding experiment is carried out with and without ROS present; for example, an ELISA is used to assess binding to the desired receptor with hydrogen peroxide added or not. The receptor of interest is coated on a high binding plate and blocked. Four samples are then tested for binding: 1) liposomes without a second PEG corona, without added peroxide, 2) liposome without a second PEG corona, with added peroxide, 3) liposomes with a second PEG corona, without added peroxide, 4) liposomes with a second PEG corona, with added peroxide. The first sample is a positive control for binding, as there is no additional PEG corona or layer concealing the targeting group. The second sample is a control for the effect of the peroxide. The third sample should illustrate decreased binding as a result of the additional PEG corona. The fourth sample should illustrate an increase in binding vs. the third sample as the ROS results in loss of the additional PEG corona. Binding is detected by addition of the receptor protein conjugated to HRP, with HRP producing an amplified colorimetric response upon addition of substrate. Carrying out this ELISA with multiple concentrations of liposome samples will provide binding curves that can be compared to assess the relative binding affinity of each liposome sample.

Efficacy is tested in vivo with mouse models of ROS producing cancers. A cancer cell line of interest is cultured and injected into mice. Liposomes with and without the second, encapsulating, ROS-responsive PEG corona would be injected into tumor bearing mice mice, along with untargeted liposomes. The liposomes are labeled with a dye or other tracking molecule to enable analysis of their targeting ability, i.e., biodistribution and tumor targeting. Fluorescence can be used as a readout (IVIS imaging). Necropsy is used to look at tissue-specific localization at various time points of interest. Comparisons between the untargeted, targeted/non-ROS responsive, and targeted/ROS-responsive liposomes indicates the efficacy of this method for targeting ROS-producing cancers.

What is claimed is:
1. A method of treating a subject, the method comprising:
administering to the subject a pharmaceutical composition, wherein the subject has cancer characterized by production of reactive oxygen species and wherein the pharmaceutical composition comprises:
an encapsulated liposome comprising:
a lipid bilayer with a first polyethylene glycol (PEG) corona, wherein the first PEG corona further comprises a targeting molecule,
a second PEG corona reversibly linked to the first PEG corona, wherein the reversible links comprise a boronic ester bond, and
one or more active agents, wherein at least one of the one or more active agents is a chemotherapeutic agent; and
a pharmaceutically acceptable carrier.
2. The method of claim 1, wherein the includes neoplasms or tumors, lymphoma, or leukemia characterized by the production of ROS.
3. The method of claim 1, wherein the boronic ester bond is formed from a linker comprising an aryl boronic acid, a phenylboronate, a pyridylboronate, or a cyclohexylboronate.
4. The method of claim 1, wherein the boronic ester bond is formed from a linker selected from the group consisting of 4-bromomethylphenyl boronic acid pinacol ester, 3-(N, N-dimethylamino)phenyl boronic acid, 2,4-dichlorophenylboronic acid, 4-aminocarbonylphenylboronic acid, 3-chlorophenylboronic acid, 4-hydroxyphenylboronic acid, 4-propylphenylboronic acid, 3-[(E)-2-nitrovinyl)phenylboronic acid, 4-chlorocarbonylphenylboronic anhydride, cyclopenten-1-ylboronic acid, 2-bromopyridine-3-boronic acid, 2,4-ditert-butoxypyrimidin-5-ylboronic acid, 2,4-bis(benzyloxy)pyrimidine-5-boronic acid, 5-phenyl-2-thienylboronic acid, and 5-formylthiophene-3-boronic acid.

* * * * *